United States Patent [19]
Ficht et al.

[11] Patent Number: 5,310,649
[45] Date of Patent: May 10, 1994

[54] METHOD FOR DETECTING SPECIES AND BIOVARS OF BRUCELLA

[75] Inventors: Thomas A. Ficht; Blair A. Sowa; L. Garry Adams, all of College Station, Tex.

[73] Assignee: Texas A & M University System, College Station, Tex.

[21] Appl. No.: 527,017

[22] Filed: May 22, 1990

[51] Int. Cl.$^5$ .............................................. C12Q 1/68
[52] U.S. Cl. ..................................... 435/6; 436/50.1; 436/811; 935/78
[58] Field of Search ...................... 435/6, 91, 29, 34; 436/501, 811; 935/77, 78; 536/23.7

[56] References Cited

U.S. PATENT DOCUMENTS 4,358,535  11/1982  Falkow et al. ........................... 435/5
4,683,202   7/1987  Mullis ..................................... 435/91

OTHER PUBLICATIONS

Embase Abstract No. 89259898, Ficht et al, Infect. Immun. (USA), 1989, (3281-3291).
Hudson et al., J. Mol. Biol. (1984) 180, 1023-1051.
Raitio et al., The EMBO Journal, vol. 6, (9) (1987), 2825-2833.
Alardet-Servent, et al., 1988, J. Bacteria 170: 4603-7, "DNA Polymorphism in Strains on the Genus Brucella".
Alton, 1988, Techniques for the Brucellosis Laboratory, Chapter 1, pp. 13-61.
Farrell, I. D., 1974, Res. Vet. Sei., 16: 280-286, "The Development of a New Selective Medium for the Isolation of *Brucella abortus* from Containated Sources".
Ficht, T. A., et al., 1988, Infection and Immunity, 56: 2036-2046, "A 36-Kilodalton *Brucella abortus* Cell Envelope Protein is Encoded by Repeated Sequences Closely Linked in the Genomic DNA".
Ficht, T. A., et al., 1989, Infection and Immunity, 57: 3281-3291, "DNA Sequence and Expression of the 36-Kilodalton Outer Membrane Protein Gene of *Brucella abortus*".
"Isolation Rate of *Brucella abortus* from Cattle" Ladwig, V. D., 1968, Iowa Vet. 39: 9-14, Card Brucellosis Test—Swine.
Moriera-Jacob, N., 1963, Nature, 197: 406, "In vitro species (or Type) Transformation among Strains of Brucella".
Nicoletti, P. and Carlsen, W. B., 1981, Am. Vet. Res., 42: 1494-1497, "Indirect Hemolysis Test in the Serodiagnosis of Bovine Brucellosis".
O'Reilly, D. J. and Cunningham, B., 1971, Vet. Rec. 88: 590-594 "An Assessment of the Brucellosis Cart Test".
Saiki, R. R., et al., 1988, "Primer-Directed Enzymatic Amplification of DNA with a Thermostable DNA Polymerase".
Shibata, S., et al., 1962, Nat. Inst. Anim. Hlth. 2: 1014 "A Possibility of Variation In *Brucella Abortus* From Type II to Type I".
Timbs, D. V., et al., 1978, N. Z. Vet. J. 26: 52-56, "The Use of Automotive Complement Fixation Techniques in the Brucellosis Eradication Scheme".
Verger, J.-M., et al., J. Sys. Bacterial 35: 292-295, "Brucella, a Monospecific Genus as Shown by Deoxyribonucleic Acid Hybridication".

*Primary Examiner*—Amelia Burgess Yarbrough
*Attorney, Agent, or Firm*—Pravel, Hewitt, Kimball & Krieger

[57] ABSTRACT

A method for detecting Brucella infection in an animal which is reliable, rapid, and able to identify species and biovars of Brucella. The detection method includes the amplification of the omp2 gene locus of Brucella and analysis of restriction digestion fragments specific to Brucella and to individual species and groups of biovars of Brucella.

19 Claims, 7 Drawing Sheets

B. ABORTUS OMP 2
LENGTH OF DNA: 3436 BP.

```
FIRST NT.
    +1  GGATCCGAGC CATGCCTTTC AGCACGACAT CCCGGCCATC GACATAAAAT CCCGCCCAGA CATAGGGTTC CAGCGCCTTT GCCGTCTGTT CGGCAATATC
  +101  GGTTTCAACC CGGTCAGCGC CGAACCAGAG CGCCAGGCCG TCAGGCACCG CCAGTCCAGG TGAGACAAGG CCAGAACCAT TTTTTCATGC TGCTTTGCTC
  +201  CGTTTCAGGC GATCTTCCGC GACCCCTGTA GAAAGACTGC GGTCAGCATA AAAAGCAAGC ATCTGATGCT GCACGAGGGC AACAAAAAAA CCGGCATTTC
  +301  TGCCGGTTTC TGTATCCAAT CCGTAATGGA TTAGAACGAA CGCTGGAAGC GAACGATACC GCCCCAAGCA TTGTCTTCAG CAACGGTGTT CTTCCACTCG
  +401  CCACCAAACT TGGTGTAGGA AACTTCCGGC GTAACGGTGA AGCCAGGAAC CAGTTCGTAA GCAACGTTAG CCGTAACTGC CGTCTTGCCC CAGTCGTCAT
  +501  GCGCAGCCTG CAGGTTGAAG GCAGCCTTCT GCGTAGCCTG ATACTTCAGA CCACCCCAGA CAGCCCAATC GCCGCCCCAC TGGCCGTAGT TCTGATCCGG
  +601  CGTAGCAGCG GACGAATATG CGCCCTGCAA CCAAACCGAG AACTGGTCGG TGATGTTGAC GTCGCCACGA ACCTTGGCAG CCCATTCTTC TATGACCGAG
  +701  TCATAGGCAA CAACACCAGC GATCGAACCC CAGCCGCCAG CATACTTCAG GCCGCCAACA ACGTCAGGCA TGTAGCCGTC GATGTGGTAG TTGGTCGTGC
  +801  CAGTGTAACC ACCGTCGTTG TCGCCACCCT GTTCGAGAGC GATCACAGCC GAGAAGCCGT TTCCGCCAGT GAAGGTGTAC GAGATCTTGC CGGTGCGGTA
  +901  GGAGCCAGCC GAGATCACGT CATCGTTGAT GACATCGCCG AGGTAACCGG TGAAGGTATG GAATTCCGAT TCATCGATAC CAACGCGCAG ACCACCGAGC
 +1001  TGGATATACG CGAACTCCAT GACGGTGCCG CTGCTGGTTT CATTACCATA TTTACCATCT ACGCCCGAAT TGTTCGCAGC ATAGTTGAAG CGCAGTTCGG
 +1101  TGAAGGTCTT GAGGGTGCCG AGTTCGGTTT CCGAACCGGT GGAAACGCGG AGTGCGAAAC GAGCGCTCTT GTCCCAGCCA TTGCGGTCGG TACCGGAGTA
 +1201  AACGTCATCG CCGCCCTTTA CGTCGTAACG GACGTAACCA TGGACGCGCA GGCAGGTTTC GGTGCCCGGA ATGTAGAAGT AGCCAGCGCC GTAAGCGTCG
 +1301  CAAACGCGGA CATATTCAAC GGCTTCGGGC TCTGGCGCGA CGATTGCGTC GGCAGCCTGA GCGCCGGAAG CTGCAACCAG AGCTGCAGCG GAGCCAAGGA
 +1401  GAAGGCTCTT GATGTTCATT TCTGACCTCC AGTCAAAGTT AAAAATGGGT CTGGGCATTC TGATTTGGCT GAAGGACAAC CTGTCCCCAT CCCCTAATTG
 +1501  AAAAAGTCGC CCCGAAGCGC TCCTTCTTCT GAAAGTGAAG ATACTCGCCC ATTTATTCGT TTCAACATCG AATATGTTCT CACAACCTTT ATGGTGCTGC
 +1601  TATGAAGGGC AGTTGTTGCA GAAATGACAC GAAATTACCT GCTTTAGCTC GGCGGATTCA TGCTTTATTA ACATAAGTGA ACGCGAATTA ACCGATGTTA
 +1701  ACGTTTGAAA ATGCAAGTTT TTTAGGATCG CCTGCAGAAT AAAGCCGCGA ATCTTTCGTC GAAACAGCCC TTAACGGAAT ATGTCGGCAA GGTGGCAAGA
 +1801  ATCGTCTGAA CGGAGAGCAG AAACCTCGAA TCCGTTTCAT TTAATAAGGG CAAGTGCGTG CCGGTGCTAA ATTGTGGGCC TTTTTAAGCG CGCCATATAT
 +1901  ATAAAGAGAA TAATCCGCAG GAAATTTTAC CAGTTAATGC GTAAATCGCT TGAAATGCCC AGGCGTACCG GTTATCTCGC CTTTACCGGA GAGGTGGCCG
 +2001  AGTGGTCGAA GGCGCTCCCT GCTAAGGAGT AGACCTCAAA GGTCTCGTGG TTCGAATCCC ATCCTCTCCG CCAGTTTTTC CAATATCCCA GCAATCTTAT
 +2101  GTGTTCGACG CGCTTGATTT CATACGGAAT CGGCTTTACC CCTCGCGCAC TGAATCTCTG TTTTTCCAGG CTACGAATCC AGAAAACAAG CAAGCCATTG
 +2201  ATAAGTAATG GCTATTCAAA ATTCTGGCGA TTCTTGACTG GAGGTCAGAA ATGAACATCA AGAGCCTTCT CCTTGGCTCC GCTGCAGCTC TGGTTGCAGC
 +2301  TTCCGGCGCT CAGGCTGCCG ACGCAATCGT CGCGCCAGAG CCCGAAGCCG TTGAATATGT CCGCGTTTGC GACGCTTACG GCGCTGGCTA CTTCTACATT
 +2401  CCGGGCACCG AAACCTGCCT GCGCGTCCAT GGTTACGTCC GTTACGACGT AAAGGGCGGC GATGACGTTT ACTCCGGTAC CGACCGCAAT GGCTGGGACA
 +2501  AGGGCGCTCG TTTCGCACTC ATGTTCAACA CGAATTCGGA AACCGAACTC GGCACACTCG GCACCTATAC TCAGCTGCGC TTCAACTACA CCAGCAACAA
 +2601  TTCACGTCAT GATGGCCAAT ACGGCGATTT CAGCGATGAT CGTGATGTCG CTGATGGCGG CGTAAGCACC GGCAAGATCG CCTACACCTT CACCGGCGGA
 +2701  AACGGCTTCT CGGCTGTGAT CGCTCTCGAA CAGGGTGGCG AAGACGTTGA CAACGATTAC ACGATCGACG GTTACATGCC GCACGTTGTT GGCGGCCTGA
 +2801  AATATGCTGG CGGCTGGGGT TCGATCGCTG GTGTTGTTGC CTATGACTCG GTCATCGAAG AATGGGCTAC AAAGGTTCGT GGCGACGTCA ACATCACCGA
 +2901  CCGGTTCTCG GTATGGCTGC AGGGCGCATA TTCGTCCGCA GCGACGCCGA ACCAGAACTA CGGTCAGTGG GGCGGCGATT GGGCTGTCTG GGGTGGTGCA
 +3001  AAGTTCATTG CCCCCGAAAA GGCAACCTTC AATCTGCAGG CTGCGCATGA CGACTGGGGC AAGACCGCAG TTACCGCCAA CGTCGCTTAT CAGCTCGTTC
 +3101  CCGGATTCAC CATTACGCCG GAAGTTTCCT ACACCAAATT TGGTGGCGAG TGGAAAGACA CCGTTGCTGA AGACAATGCC TGGGGCGGTA TCGTTCGCTT
 +3201  CCAGCGCTCG TTCTAATCAG ATCGACGTTA AGCATAGGGC GCCAACGGTT TCCCGTTGGC CGCCGGTTCA TTTGAAACAG CGTTCACGAA AGCGTGAGAA
 +3301  TCGATTCTTC CGGAATGGGG ATTCCAGGCG GATCGACAAT TGAGGGAATT GCGGGGACGA CAAAAAGCTG GGGGCAACCG GGGGGTCTTG TAAAGGATTG
 +3401  AGCCATGTCT CCATAAAGTT AGCCTACTTA TCTTGT
```

FIG. 7

OLIGONUCLEOTIDE PAIRS TO AMPLIFY BRUCELLA OMP2 GENE

| ID.NO. | SEQUENCE | AMPLIFIED GENE |
|---|---|---|
| 47 | CGC GAA CTC CAT GAC GGT GCC GC | omp2b |
| 41 | CCT TGG CTC CGC TGC AGC TCT GGT | |
| 32 | CAG GCG ATC TTC CGC GAC CCC | omp2b |
| 33 | GGG GAT GGG GAC AGG TTG TCC | |
| 51 | TGG GTC TGG GCA TTC TGA TTT GGC TG | flanking |
| 50 | TCG CCA GAA TTT TGA ATA GCC ATT AC | |
| 41 | CCT TGG CTC CGC TGC AGC TCT GGT | omp2a |
| 46 | CGT TGT CAA CGT CTT CGC CAC CC | |
| 34 | CCG GCG GCC AAC GGG AAA CCG | omp2a |
| 35 | CGG CTT TAC CCC TCG CGC AC | |

METHOD FOR DETECTING SPECIES AND BIOVARS OF BRUCELLA

FIELD OF THE INVENTION

This invention relates to a method for the diagnostic detection of the pathogenic bacterium Brucella. and more specifically to a method which can distinguish between species and biovars of Brucella.

BACKGROUND OF THE INVENTION

Brucella is a genus of pathogenic bacteria which cause acute or chronic illness in many animal species, including humans and cattle. Six species of Brucella and multiple biovars have been characterized by phenotypic methods, although such methods are not always reliable. The six species and multiple biovars of Brucella may also be characterized by their natural host and a strain's geographical origin (See Table 1), however, a species may infect an animal other than its natural host, and a single strain may now be found in multiple geographic locations.

Early detection and characterization of the species or biovar of the infecting Brucella organism would be of great value in medical and veterinary practice. Rapid and reliable detection of Brucella infection is important to permit removal of infected cattle from a healthy herd and prevent the spread of the disease. Characterization of the species or biovar of Brucella would provide epidemiological data to determine the source of the infection.

TABLE 1

| SPECIES | BIOVAR | STRAIN | HOST | ORIGIN |
|---|---|---|---|---|
| *B. abortus* | 1 | 19 | | U.S. |
| | 1 | 2308 | cattle | U.S. |
| | 1 | RB51 | d.2308[a] | U.S. |
| | 1 | 45/20 | d.45/0 | England |
| | 2 | ATCC 23449 | cattle/ | England |
| | 3 | ATCC 23450 | bison | Uganda |
| | 4 | ATCC 23451 | " | England |
| | 5 | ATCC 23452 | " | England |
| | 6 | ATCC 23453 | " | Africa |
| | 7 | ATCC 23454 | " | |
| | 9 | ATCC 23455 | " | England |
| *B. melitensis* | 1 | ATCC 23456 | goat | U.S. |
| *B. suis* | 1 | ATCC 23444 | pig | U.S. |
| *B. neotomae* | | ATCC 23459 | desert wood rat | U.S. |
| *B. canis* | | ATCC 23365 | dog | U.S. |
| *B. ovis* | | ATCC 25840 | sheep | Africa |

ATCC - American Type Culture Collection, Bethesda, Maryland.
d. - derivative

Heretofore, standard serological tests used to detect Brucella have required several weeks time to complete and have not been able to distinguish between species of Brucella. The methods currently available to identify species of infecting Brucella require the isolation of bacteria on selective media followed by quantitative analysis of phenotypic properties of the organism. Phenotypic characterization may be based on such features as lipopolysaccharide antigens, phage typing, dye sensitivities, $CO_2$ requirements, $H_2S$ production, and metabolic properties. Such methods are time consuming (requiring 1-4 weeks) and are unreliable. (see Alton, 1988, *Techniques for the Brucellosis Laboratory*; Moriera-Jacob, 1963, *Nature* 197:406; Shibata, 1962, *Nat. Inst. Anim. Health Q.* 2:10-14) Time delays in obtaining test results and uncertainty due to unreliable test results can result in great economic losses. Suspect animals may require quarantine or may contaminate healthy animals in the herd during the waiting period.

Identification of Brucella species using DNA probes has not previously been possible, due to the high degree of inter-species DNA homology (approximately 90%).

There remains a great need for a rapid and accurate method for detecting the presence of pathogenic Brucella organisms in a suspect animal. It is also greatly desirable that such a detection method have the ability to distinguish between and identify the species and/or biovars of Brucella.

SUMMARY OF THE INVENTION

The method of the present invention solves the problems of the prior art methods by providing a rapid, sensitive, and accurate diagnostic method for the detection of Brucella and, more specifically a diagnostic method which is able to distinguish between species and biovars of Brucella.

It has now been found that the opm2 gene locus is conserved in all species of Brucella. Rapid detection of Brucella is achieved by identification of the conserved omp2 gene locus.

It has also been found that genetic variation at the omp2 gene locus of Brucella correlates with established species designations, and that this genetic variation may be used as a stable diagnostic marker for particular species of Brucella. Differentiation between species and biovars is based upon analysis of restriction fragment length polymorphism in the omp2 gene locus of Brucella.

A preferred embodiment of the method of the present invention includes amplification of the omp2 gene locus. The amplified omp2 gene locus may then be analyzed directly by electrophoretic separation, dot blot or Southern Blot analysis to enable diagnosis of Brucella infection. Alternatively, restriction digestion of the amplified omp2 gene releases fragments which may be analyzed, for example by gel electrophoresis, and the restriction fragment pattern used to detect the presence of Brucella and to identify the species or biovar of Brucella.

DESCRIPTION OF THE DRAWINGS

FIG. 1 is a partial restriction map of the omp2 locus of the different Brucella species and biovar groups.

FIG. 2 shows the top strand of the DNA sequence encoding the *Brucella abortus* omp2 gene locus with solid lines depicting oligonucleotides useful in amplifying portions of the omp2 gene locus.

FIG. 3 is a partial restriction map of the omp2 locus of the *Brucella abortus.*

FIG. 4 is a Southern Blot of Brucella genomic DNA digested with Bam HI and hybridized with a labeled Bam HI fragment containing the omp2 gene locus of *B. abortus.*

FIG. 5 is a Southern Blot of Brucella genomic DNA digested with Pst I and hybridized with a labeled Bam HI fragment containing the omp2 gene locus of *B. abortus.*

FIG. 6 is an agarose gel stained with ethidium bromide showing the presence of the amplified omp2 gene in Brucella infected versus non-infected cattle.

FIG. 7 is a listing of oligonucleotides useful in the present invention.

DETAILED DESCRIPTION OF THE INVENTION

According to the method of the present invention, animal fluids or tissues may be tested for the presence of Brucella, and the species and biovar of Brucella infecting the animal may be rapidly and accurately detected. Animal fluids and tissues including blood, urine, milk, semen, vaginal secretions, rectal secretions or other available tissues may be collected and used as the test sample, despite the presence of complex, non-Brucella DNA. The live bacteria in the sample are killed, for example by heating to 68° C. for approximately 1 to 2 hours. The cells of the sample are then lysed to release DNA, for example, by heating to approximately 95° C. for approximately ten minutes or by repeated freezing and thawing of the cells. It may be desirable to immobilize the released DNA on a solid support in order to concentrate the DNA. For example, the DNA released by the lysed cells may be collected and concentrated in an agarose gel, or on a nitrocellulose filter.

A desired gene sequence in the DNA released from the lysed cells is then amplified, preferably through 30 to 50 cycles, by means of standard liquid polymerase chain reaction (PCR) using commercially available cyclers or manually in changing water baths. The PCR method is known in the art, and is described, for example, in Saiki et al, Science 239:487–491, 1985, which is hereby incorporated by reference. In general, the PCR amplification method includes the hybridization of a pair of oligonucleotide primers to a segment of DNA. The oligonucleotide primers are designed to anneal to the DNA sequences flanking the target gene sequence that is to be amplified, with one oligonucleotide upstream and one downstream of the target sequence, on opposing DNA strands. During each amplification cycle, DNA strands are separated, for example by heating, priming oligonucleotides are annealed, for example by cooling the heated DNA in the presence of the oligonucleotides, and the primers are extended using DNA polymerases and adding nucleotides to the end of each primer to make copies of the target DNA sequence. This process is repeated through approximately 30–50 amplification cycles, geometrically increasing the number of copies of the target gene sequence.

Figure 1:
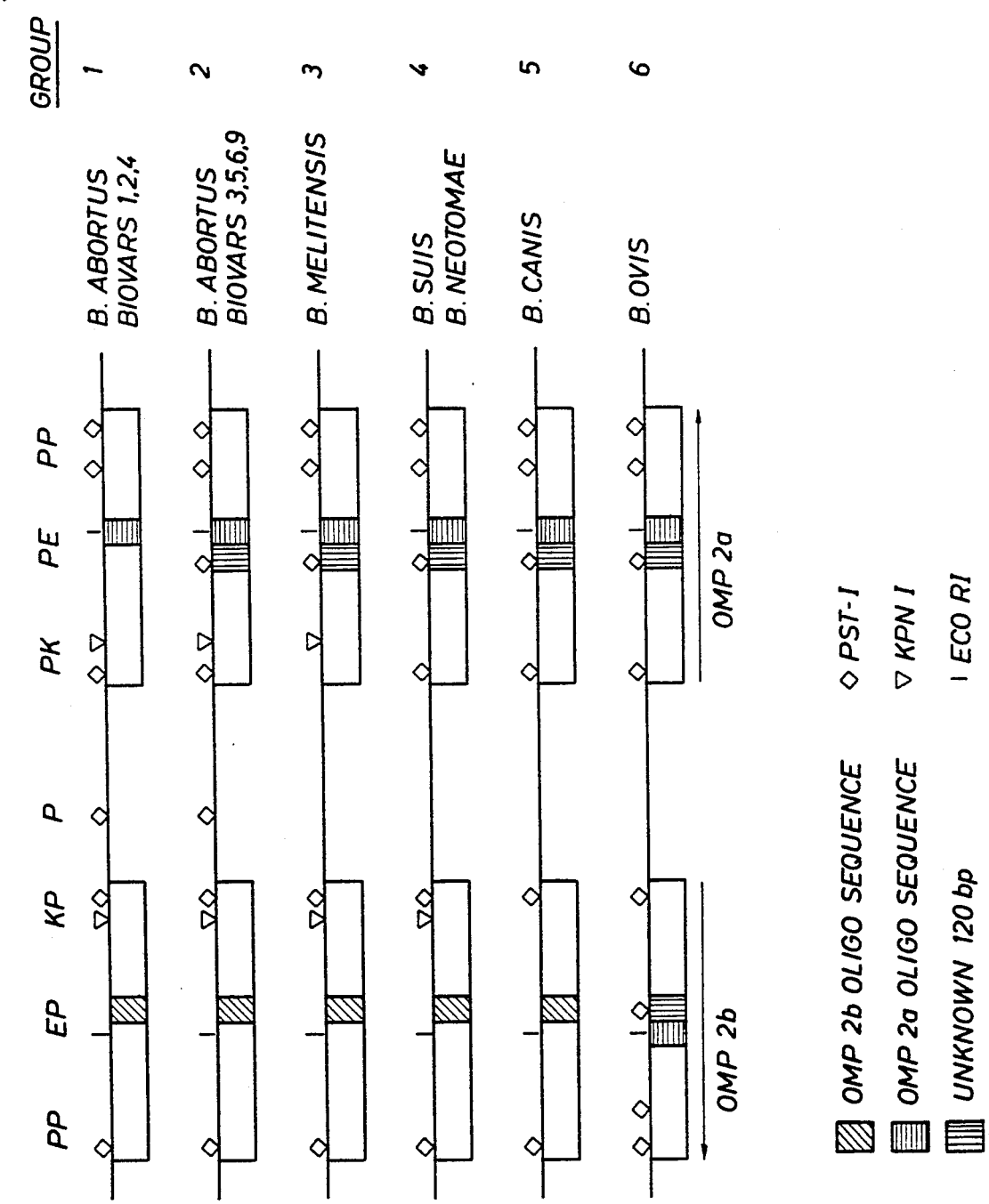

Specific oligonucleotides are used to prime the amplification at the omp2 gene locus. As shown in FIG. 1, the omp2 gene locus includes the omp2a and omp2b genes as well as flanking and intervening gene sequences. The DNA sequence of the B. abortus omp2 gene locus is shown in FIG. 2. Specific oligonucleotide pairs designed to hybridize to specific gene sequences of the omp2 gene locus permit amplification of a desired gene sequence of the omp2 gene locus.

Examples of oligonucleotides useful in the present invention include those listed in FIG. 7, and those shown in FIG. 2.

The amplified DNA may be analyzed directly by dot blot analysis using a labeled omp2 gene probe, by competitive hybridization analysis using radiolabeled oligonucleotide probes, or by separating the amplified DNA, for example, using agarose gel electrophoresis and ethidium bromide staining or Southern Blot analysis to detect the amplified gene sequence. The presence of the amplified omp2 gene indicates the presence of Brucella organisms in the test sample.

In a preferred embodiment, the amplified DNA may first be digested with specific restriction enzymes to generate restriction fragments characteristic of the omp2 gene locus prior to analysis by separation and staining or hybridization to specific omp2 gene probes. Proper selection of the restriction enzyme may result in fragments displaying an electrophoretic pattern characteristic of the Brucella omp2 gene in all species of Brucella. Alternatively, the selection of restriction enzymes may result in fragments displaying restriction fragment length polymorphism (RFLP), for example, in the omp2a gene and flanking sequence of Brucella.

A preferred restriction enzyme which can be used to detect the omp2 gene in all species of Brucella is Bam H1. Restriction digestion of genomic or amplified Brucella DNA using Bam HI releases a characteristic 6.5 kb fragment containing the omp2 gene.

Preferred restriction enzymes which can be used to identify the particular species or biovar of the infecting Brucella organism include PstI and KpnI. Digestion of the amplified omp2 gene locus with PstI and/or KpnI results in restriction fragments displaying a unique electrophoretic pattern in agarose gels for *B.abortus, B. melitensis, B. canis,* and *B.ovis.* The restriction fragment patterns for *B. suis* and *B. neotomae,* while distinct from the other 4 Brucella species, are not distinguished from each other using these digestive enzymes. Biovars 1, 2, and 4 of *B.abortus* may also be identified based upon the size of the PstI restriction fragments.

The pattern of restriction fragments may be visualized in the electrophoretic gel by staining, for example, with ethidium bromide, which has a sensitivity in the range of 0.1–1.0 μg DNA. Alternate the amount of DNA is limited, i.e., 0.0–0.1 μg DNA, Southern Blot or dot blot analysis with omp2 DNA probes can be used.

EXAMPLES

EXAMPLE 1

Conservation of the omp2 Gene Locus in Species and Biovars of Brucella

*B.abortus* smooth strains 19 and 2308 were obtained from Dr. Billy Deyoe at the National Animal Disease in Ames, Iowa. *B.abortus* biovars 1–7 and 9, *B.suis, B.canis. B.neotomae, B.melitensis,* and *B.ovis* were obtained for the American Type Culture Collection, in Bethesda, Md. (See Table 1). Strain identification was confirmed by standard biovar analysis (see Alton, 1988). Brucella strains were cultivated on either Brucella agar or tryptic soy agar (Difco Laboratories, Detroit, Mich.). *E. Coli* cells were grown as described in Ficht, 1988, *Infect. Immunol.* 56:2036–2046.

Brucella cells were grown on agar plates at 37° C. for approximately 48 hours. Cells were washed off the plates in 5 ml of phenol/saline (0.1% w/v and 0.85% w/v, respectively). The cells were killed by incubation for 1–2 hours at 68° C. and pelleted by centrifugation at 5000 rpm for 20 minutes. The cell pellet was resuspended in 5 ml buffer A (10mM TrisHCl, pH 7.6, 1 M NaCl) at room temperature, pelleted again, and resuspended in a final volume of 2 ml buffer A. The cell suspension was warmed to 42° C. and diluted with an equal volume of a solution containing 1 % W/v low melting point agarose (Bethesda Research Labs,—Bethesda, Md.) in sterile water. Aliquots (100–200 μl) of this mixture were poured into molds to form agarose blocks and chilled on ice. The blocks were transferred to Eppendorf tubes containing an equal volume of lysis buffer (6 mM Tris-HCl, pH 7.6, 1 M NaCl, 100 mM EDTA, pH 7.5, 0.5% w/v Bri-58 (Aldrich, Milwaukee, Wis.), 0.2% w/v sodium deoxycholate, 0,5% w/v sodium N-lauroylsarcosine) made from sterile stock solutions and filter sterilized following the addition of detergents. This solution was supplemented just prior to use with 1 mg/ml lysozyme and 20 µg/ml RNase A (10 mg/ml stock in sterile dH$_2$O heated to 80° C. for 20 minutes). The cell suspension was then incubated in the lysis buffer overnight at 37° C. The following day the lysis buffer was removed and an equal volume of ESP buffer ( 0.5 M EDTA, pH 9-9.5, 1% w/v in sodium lauryl sarcosinate, and 1.0 mg/ml proteinase K preincubated for 2 hours at 37° C.) was added. The mixture was incubated for 24-48 hours at 50° C. The gel block was then washed in 4 changes of TE buffer (50 mM Tris-HCl, 0.1 mM EDTA, pH 7.5) containing 1 mM phenyl methyl-sulfonyl fluoride (PMSF) for 4 hours at room temperature. The gel block was then washed twice for 4-16 hours with Bam HI restriction enzyme buffer (as supplied by the manufacturer, Boehringer-Mannheim, Indianapolis, Ind.) The washed block was dissolved in 0.5 ml of the restriction enzyme buffer at 65° C. for 10 minutes.

Figure 3:
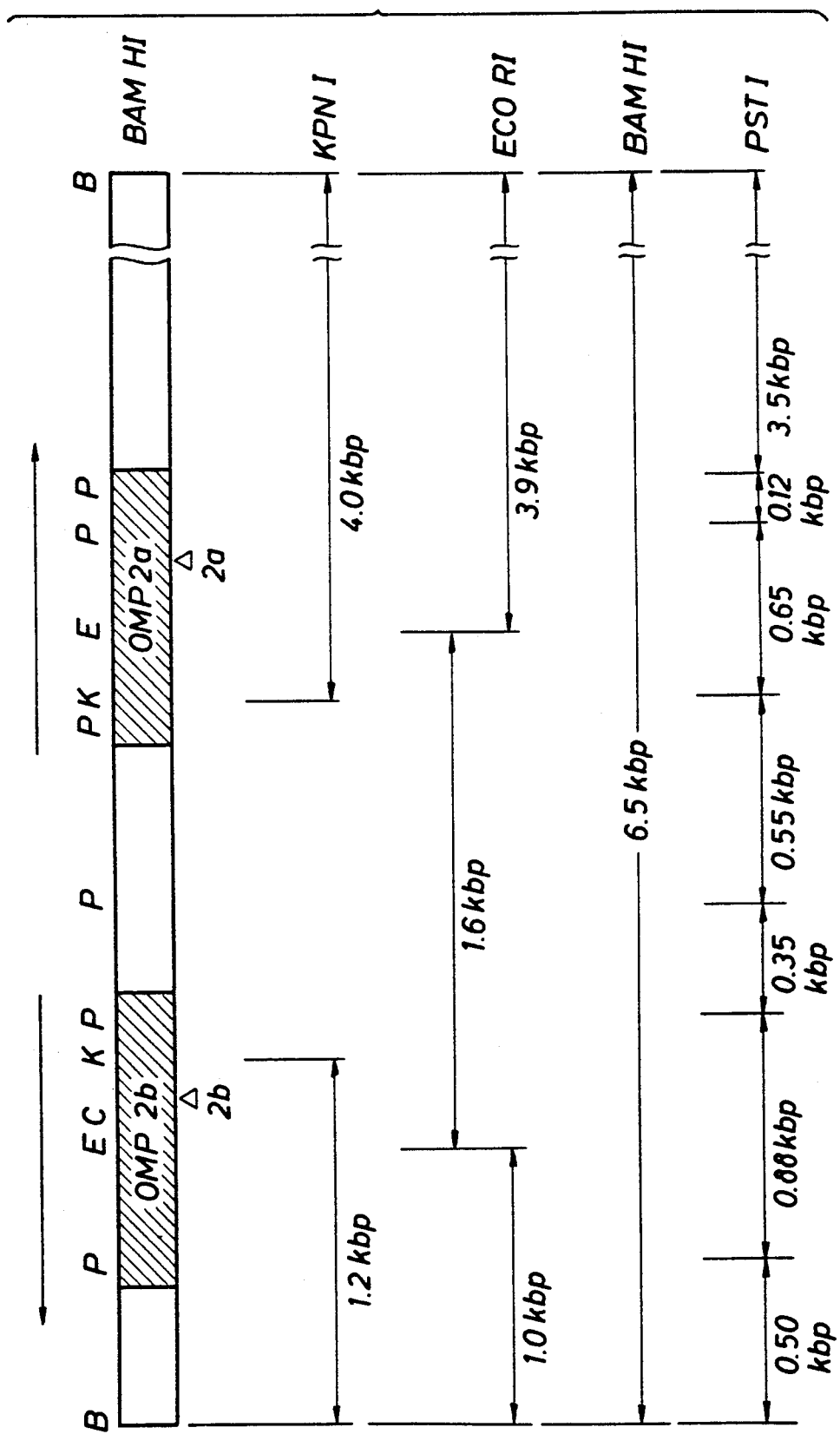
Figure 4:
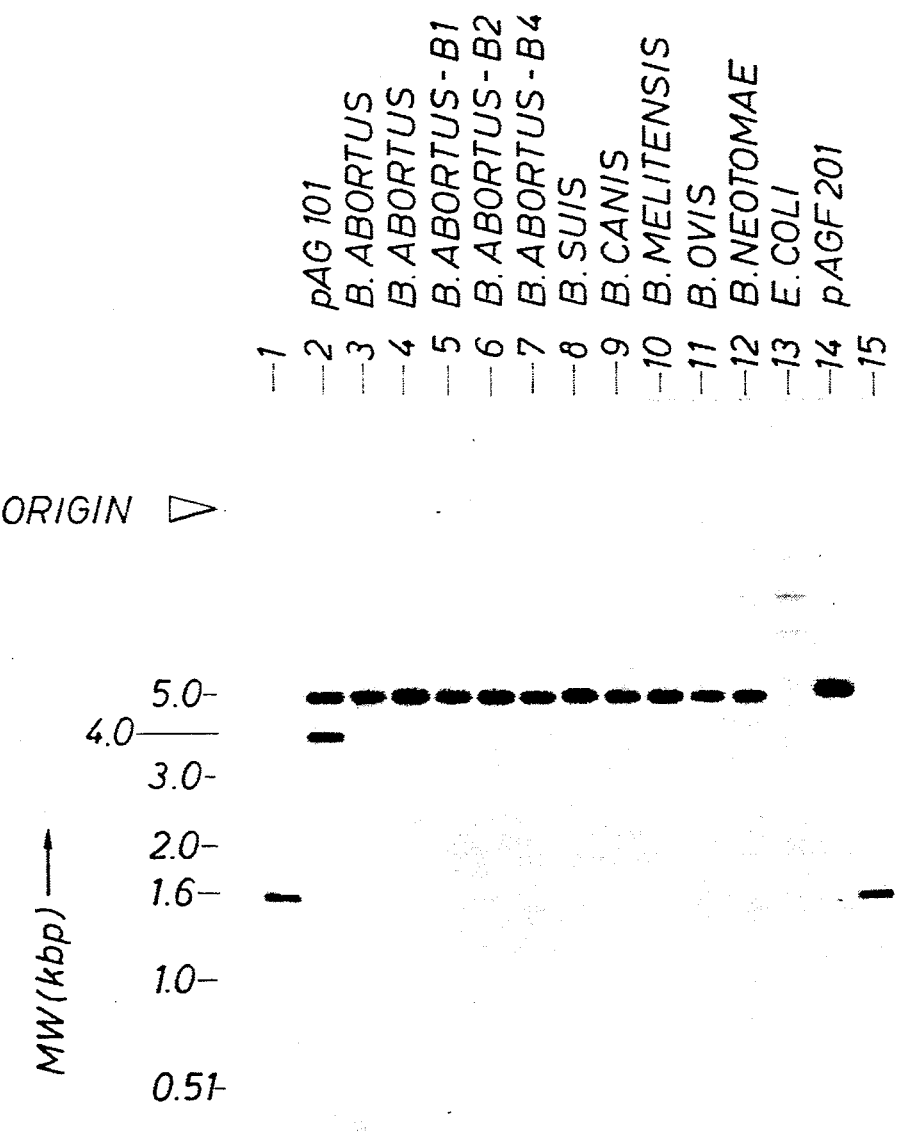
Figure 5:
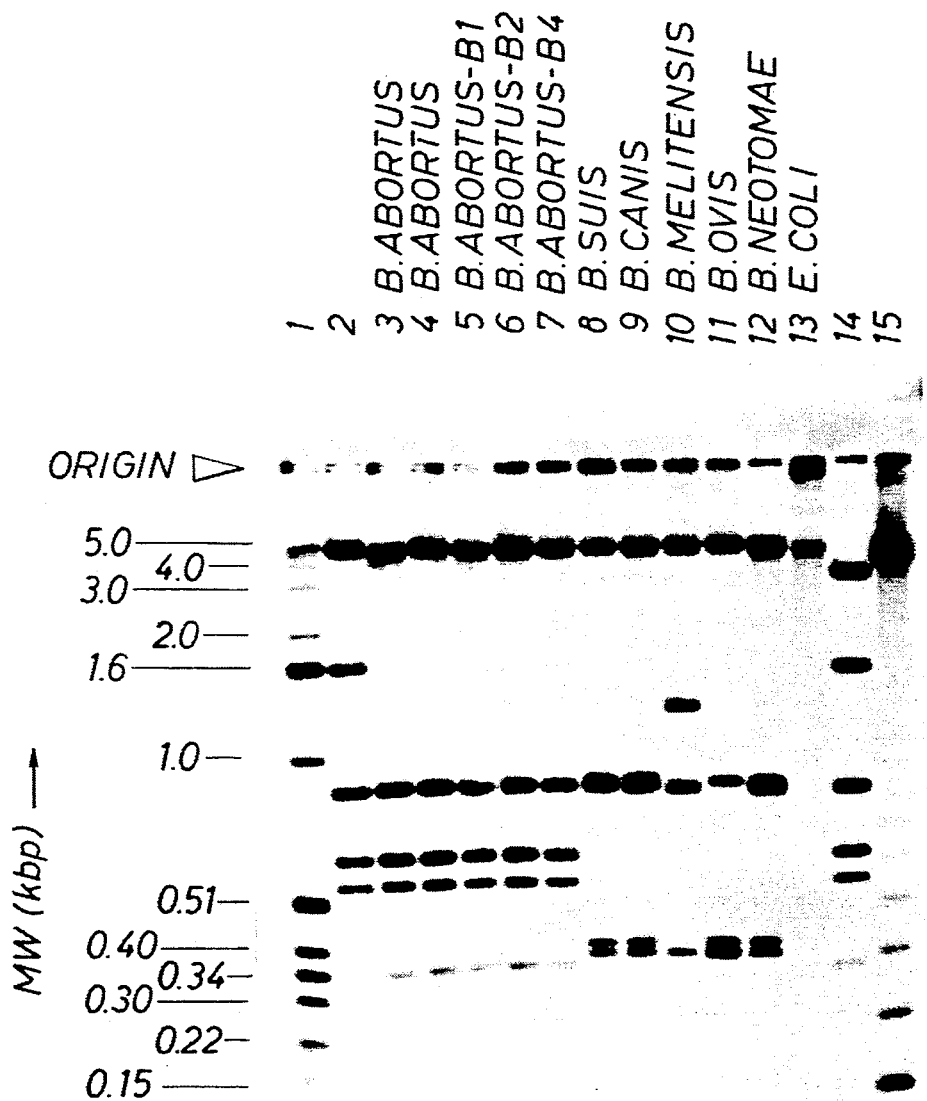
Figure 6:
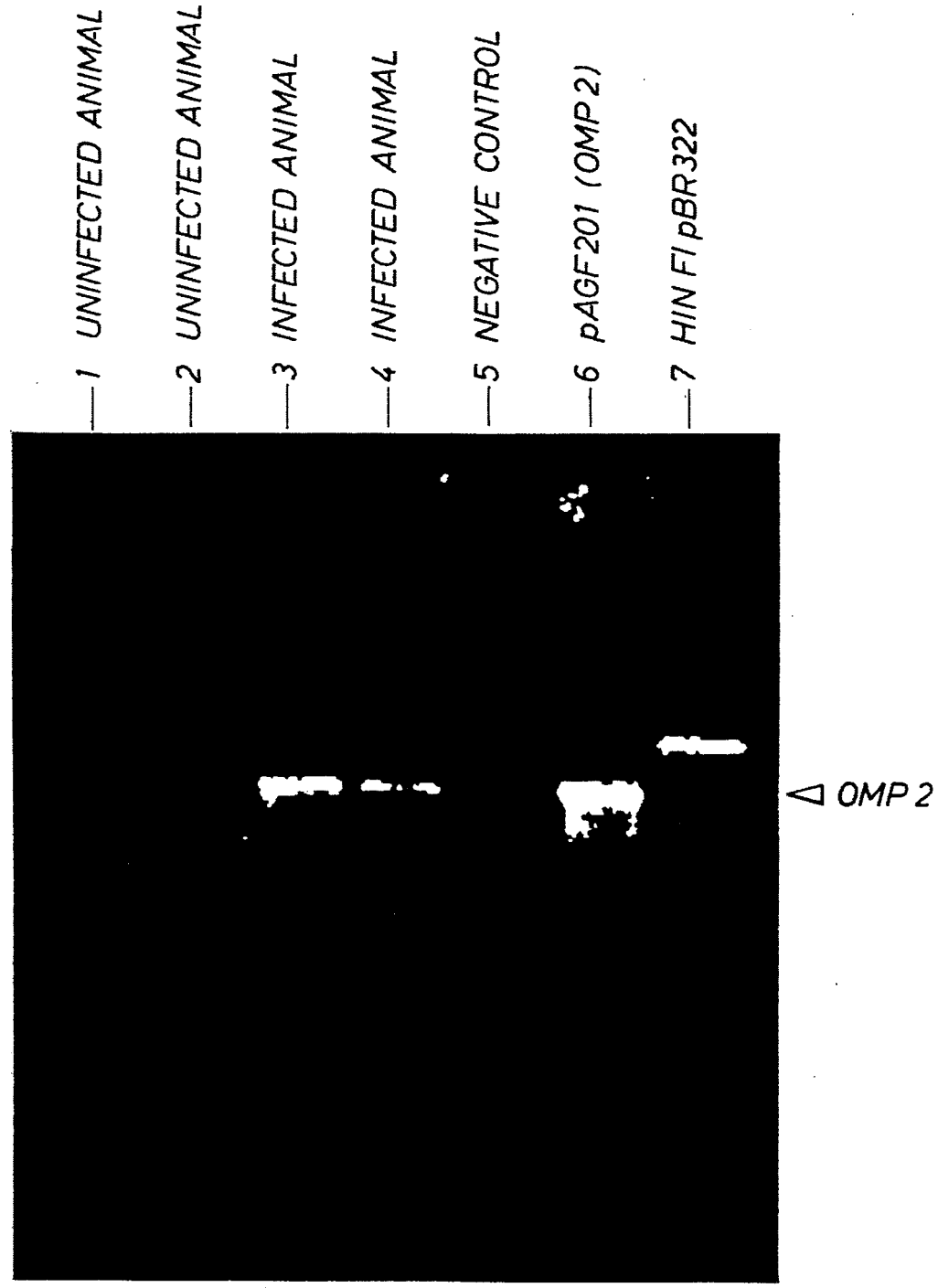

The restriction fragments were separated in a 2% w/v agarose gel. Southern Blot analysis included the transfer of the separated restriction fragments onto nitrocellulose, and hybridization with a labeled oligonucleotide probe consisting of the Bam HI restriction fragment of the *B. abortus* omp2 gene locus, as shown in FIG. 3. The results of the Southern Blot analysis are shown in FIG. 4, and indicate that all six species of Brucella and all *B. abortus* biovars tested have conserved the omp2 locus on a 6.5 kb Bam HI fragment.

EXAMPLE 2

Heterooeneity of the omp2a Gene in Species and Biovars of Brucella

Aliquots of Brucella DNA prepared for Example 1 were treated as described in Example 1, but digested with Pst I in Pst I restriction enzyme buffer (as provided by the manufacturer, Boeringer- Mannheim). Electrophoresis and Southern blot analysis were carried out as described for Example 1. The results of the Southern Blot analysis are shown in FIG. 5, and indicate that the genetic variation of the omp2 locus segregated along classical species lines, that is the Pst I restriction fragment profiles of the omp2 gene locus were distinct for different species and Biovars of Brucella. Based on Pst I restriction digestion, the species can be divided into six groups as shown in FIG. 1. Group 1 includes *B. abortus* biovars 1,2 and 4. Group 2 includes *B. abortus* biovars 3,5,6,7 and 9. Group 3 includes only *B.melitensis.* Group 4 includes *B.suis* and *B.neotomae.* Additional restriction digestion with the restriction enzyme Kpn I enabled distinction of Group 5, *B.canis* from the species of Group 4. Group 6 contains only *B. ovis.*

This data indicates that after one restriction digest with Pst I, analysis of the restriction fragments can distinguish between *B.abortus, B.ovis, B.melitensis,* and the remaining species of Brucella. Restriction fragments generated from Pst1 digestion can also distinguish between *B.abortus* biovars 1 ,2 and 4 from *B.abortus* biovars 3,5,6, 7 and 9. Additional digestion with Kpn I permits the distinctive identification of *B.canis.*

EXAMPLE 3

Detection of Brucella in Tissue Samples of Infected and Control Cattle bv Amplification of omp2 DNA Cattle (two) (mixed breed, (*Bos Taurus*×*Bos Indicus,* Montana Beaver Head Ranch, Big Hole, Mont.), at approximately 120 days gestation, were infected with $1\times10^7$ *B.abortus* S2308 organisms (obtained from Dr. Billy Deyoe, U.S.D.A. N.A.D.C.). Abomasal tissue samples were prepared from either aborted calves or live calves of the two infected animals and two non-infected control animals.

Abomasal tissue samples were obtained by necroscopy following animal sacrifice. The fetal stomach or abomasum and its contents were dissected and stored in whirlpak bags (NASCO, Fort Atkinson, Wisconsin). Portions of the abomasal samples were heated at 68° C. for 2 hours in eppendorf tubes to kill any live Brucella, and 5 μl portions were then added to amplification reactions according to the method of Saiki et al, 1985.

The standard amplification reaction was performed in a final volume of 100 μl containing 200 μM of each nucleotide (dNTP, dGTP, dCTP, dTTP), 2.5 units Taq polymerase, approximately 0.1ng template DNA and 1μM each oligonucleotide primer. The reaction buffer also contained 10 mM TRIS-HCl, pH 8.3, 50 mM KCl, 1.5 mM $MgCl_2$, and 0.01% w/v gelatin. The oligonucleotides used to prime the amplification were No. 32 and No. 33, as shown in FIG. 7, which amplified the omp2b gene of Brucella.

The DNA was amplified through 30 cycles including a 30 second melting at 94° C., annealing over 30 seconds at 62°–65° C., and polymerization at 72° C. for three minutes.

The amplified DNA was then sized in a 1–2% w/v agarose gel and stained with ethidium bromide to visualize the DNA. As shown in FIG. 6, DNA obtained from infected animals amplified the 1268 bp omp2b gene fragment characteristic of Brucella. Non-infected animals showed no amplified DNA product.

EXAMPLE 4

Detection of Brucella in Milk Samples From Infected and Control Cattle

Pregnant cattle (six) (*Bos Taurus*×*Bos Indicus,* Montana Beaver Head Ranch, Big Hole, Mont.), at approximately 120 days gestation were infected with $1\times10^7$ *B.abortus* S2308 (obtained from Dr. Billy Deyoe) organisms by conjunctival installation. Four uninfected cattle served as controls. The animals are monitored serologically for infection until abortion or the birth of a live calf. Samples collected for bacteriologic analysis are used for PCR amplification and DNA analysis of Brucella.

Blood samples are collected weekly; sera is tested by the following methods:

1. buffered Brucella antigen (Card) (O'Reilly and Cunningham, 1971, Vet.Rec. 88:590–594; Ladwig, 1968, *Iowa Vet.* 39:9–14).

2. enzyme linked immunosorbent assay (ELIZA) (Heck et al, 1980, *Am. J. Vet. Res.* 41:2082–2084).

3. rivanol precipitation plate agglutination (Huber and Nicoletti, 1986, *Am. J. Vet. Res,* 47:1529–1531).

4. automated tube (warm) complement fixation with Brucella antigens and hemolysis in gel test (Timbs et al, 1978, *N.Z. Vet. J.* 26:52–56; Nicoletti and Carlsen, 1981, *Am. J. Vet. Res.* 42:1494–1497).

Vaginal and rectal swabs, placental and quarter milk samples from all parturient cattle will be cultured for Brucella. Rectal swabs from viable calves, and pulmonary tissue, gastric contents, mediastinal lymph nodes, and rectal swabs from dead fetuses or neonates will be streaked onto semi-restrictive Brucella agar medium with 5% bovine serum and antibiotics (Farrell's Medium, Farrell et al, 1974, *Res. Vet. Sci.* 16:280-286).

Culture negative parturient principals and controls will be euthanized and at least 50 tissues will be collected, trimmed of non-lymphatic tissue, and both sides of the cut surface will be rubbed over the surfaces of Farrell's media ( 3 plates per tissue sample). Inoculated media will be incubated at least 7 days at 37° C. in 10% $CO_2$ with bacterial colonies resembling Brucella further identified and biotyped by conventional methods for comparison with results for the same animal from PCR amplification and analysis of DNA from tissue and fluid samples.

DNA obtained from blood, milk, semen, vaginal secretions, rectal secretions and tissue samples will be concentrated if necessary onto nitrocellulose filters. The DNA obtained will be amplified according to the procedure described for Example 3, using oligonucleotides which amplify specific regions of the omp2 gene locus. Amplification of the omp2b gene locus and identification of the omp2b gene as described for Example 3 will identify the presence of Brucella organisms. Amplification of the omp2a gene using the oligonucleotides No. 34 and No. 35, as shown in Table 2, followed by electrophoretic analysis of the amplified sequence will be used to determine the presence of Brucella in the test sample. Restriction digestion of the amplified DNA sequence using the enzyme Pst I will characterize the infecting Brucella species as *B.abortus* biovars 1,2,4, *B.abortus* biovars 3,5,6,9. *B.ovis, B.melitensis,* or one of the remaining three Brucella species. Restriction digestion using the enzyme Kpn I will distinguish *B.canis* from the remaining two Brucella species, *B.suis* and *B. neotomae.*

Having described the invention above, various modifications of the techniques, procedures, materials, and equipment will be apparent to those in the art. It is intended that all such variations within the scope and spirit of the appended claims be embraced thereby.

We claim:

1. A method for diagnosing Brucella infection comprising the steps of:

releasing DNA from a test sample;

releasing DNA from a test sample;

amplifying at high stringency a gene sequence of a Brucella omp2 gene locus includes omp2a gene, omp2b gene, nucleic acid sequences intervening between the omp2a and omp2b genes, and approximately 300 nucleic acids flanking the omp2a and omp2b genes; and analyzing the amplified gene sequence to detect Brucella omp2 gene sequences diagnostic of Brucella.

2. The method of claim 1, wherein said gene sequence corresponds to a region of Brucella omp2a gene.

3. The method of claim 1, wherein said gene sequence corresponds to a region of Brucella omp2b gene.

4. The method of claim 1, wherein said gene sequence is approximately 300 nucleic acids immediately adjacent to the omp2a or omp2b gene.

5. The method of claim 1, wherein said gene sequence is the nucleic acid sequence intervening between the omp2a and omp2b genes.

6. The method of claim 1, wherein said amplifying is by polymerase chain reaction.

7. The method of claim 6, wherein the polymerase chain reaction is primed with an oligonucleotide pair which anneals to the omp2 gene locus of Brucella, where the omp2 gene locus includes omp2a gene, omp2b gene, nucleic acid sequences intervening between the omp2a and omp2b genes, and approximately 300 nucleic acids flanking the omp2a and omp2b genes.

8. The method of claim 6, wherein the polymerase chain reaction is primed with an oligonucleotide pair selected from those shown in FIG. 7.

9. The method of claim 1, wherein prior to said analyzing step, the amplified DNA is digested with a restriction enzyme to generate restriction fragments characteristic of Brucella.

10. The method of claim 1, wherein, prior to said analyzing step the amplified DNA is digested with a restriction enzyme selected from the group consisting of Pst I and Kpn I, to generate restriction fragments characteristic of a Brucella species or biovar.

11. The method of claim 10 wherein the restriction enzyme is Pst I.

12. The method of claim 10 wherein the restriction enzyme is Kpn I.

13. The method of claim 1, wherein said analyzing includes dot blot analysis using labeled DNA which hybridizes to the omp2 gene locus of rucella.

14. The method of claim 1, wherein said analyzing includes electrophoretic separation of the amplified DNA and staining with ethidium bromide.

15. The method of claim 1, wherein said analyzing includes Southern blot analysis using labeled DNA which hybridizes to the omp2 gene locus of Brucella.

16. The method of claim 1, wherein said test sample is animal fluid or tissue.

17. The method of claim 16, wherein said test sample is urine, blood, milk, semen, vaginal or rectal secretions.

18. The method of claim 17, wherein said test sample is milk.

19. A method for identifying a species or bovar of Brucella comprising the steps of:

releasing DNA from a test sample;

amplifying at high stringency a gene sequence of a Brucella omp2 gene locus from the released DNA, where the omp2 gene locus includes omp2a gene, omp2b g ne, nucleic acid sequences intervening between the opm2a and omp2b genes, and approximately 300 nucleic acids flanking the omp2a and omp2b genes; and analyzing the amplified gene sequence to detect Brucella omp2 gene sequences diagnostic of a species or biovar of Brucella.

* * * * *

UNITED STATES PATENT AND TRADEMARK OFFICE
CERTIFICATE OF CORRECTION

PATENT NO. : 5,310,649

DATED : MAY 10, 1994

INVENTOR(S) : THOMAS A. FICHT, BLAIR A. SOWA, L. GARRY ADAMS

It is certified that error appears in the above-identified patent and that said Letters Patent is hereby corrected as shown below:

CLAIM 1, COLUMN 7, PLEASE DELETE LINE 52.

CLAIM 1, COLUMN 7, LINE 54, AFTER "LOCUS" PLEASE INSERT --FROM THE RELEASED DNA, WHERE THE OMP2 GENE LOCUS--.

CLAIM 13, LINE 36, COLUMN 8, PLEASE DELETE "RUCELLA" AND INSERT --BRUCELLA--.

CLAIM 19, LINE 49, COLUMN 8, PLEASE DELETE "BOVAR" AND INSERT --BIOVAR--.

CLAIM 19, LINE 56, COLUMN 8, PLEASE DELETE "OPM2a" AND INSERT --OMP2a--.

Signed and Sealed this

Thirtieth Day of August, 1994

Attest:

Attesting Officer

BRUCE LEHMAN

Commissioner of Patents and Trademarks